United States Patent
Kuybeda et al.

(10) Patent No.: US 11,373,302 B2
(45) Date of Patent: Jun. 28, 2022

(54) THERMAL CAMERA, AND METHOD THEREOF FOR EARLY DIAGNOSIS OF INFECTIOUS DISEASES

(71) Applicant: Adasky, Ltd., Yokneam Illit (IL)

(72) Inventors: Oleg Kuybeda, Portland, OR (US); Igor Ivanov, Haifa (IL)

(73) Assignee: Adasky, Ltd., Yokneam Illit (IL)

( * ) Notice: Subject to any disclaimer, the term of this patent is extended or adjusted under 35 U.S.C. 154(b) by 245 days.

(21) Appl. No.: 16/865,124

(22) Filed: May 1, 2020

(65) Prior Publication Data
US 2021/0343005 A1  Nov. 4, 2021

(51) Int. Cl.
*G06K 9/00* (2022.01)
*G01K 15/00* (2006.01)
(Continued)

(52) U.S. Cl.
CPC .......... *G06T 7/0012* (2013.01); *A61B 5/0075* (2013.01); *A61B 5/015* (2013.01);
(Continued)

(58) Field of Classification Search
USPC ....... 382/100, 103, 106, 118, 128, 162, 168, 382/173, 181, 191, 199, 219, 232, 254,
(Continued)

(56) References Cited

U.S. PATENT DOCUMENTS 6,267,501 B1 * 7/2001 Wand .................. H04N 5/2178
374/2
6,538,250 B2   3/2003 McManus et al.
(Continued)

FOREIGN PATENT DOCUMENTS

| CN | 102901516 B  | 8/2015 |
| CN | 104089627 B  | 5/2017 |
| WO | 2016055155 A1 | 4/2016 |

OTHER PUBLICATIONS

D'Angelo, "Radiometric Alignment and Vignetting Calibration," Proceedings of the ICVS Workshop on Camera Calibration Methods for Computer Vision Systems—CCMVS2007, Germany, 2007.
(Continued)

*Primary Examiner* — Seyed H Azarian
(74) *Attorney, Agent, or Firm* — M&B IP Analysts, LLC

(57) ABSTRACT

A radiometric camera and method for obtaining accurate radiometric readings of objects in a scene captured by a radiometric camera. The method comprises estimating a gamma drift coefficient based on an input thermal image, wherein the thermal image is captured by an infrared sensor; performing, based on the gamma drift coefficient and the input thermal image, a sensor temperature stabilization to provide an ambient-stabilized thermal image, wherein the ambient-stabilized thermal image is invariant to temperature changes of the infrared sensor; performing ambient calibration to estimate a scene temperature based on the ambient-stabilized thermal image; and measuring, based on the estimated scene temperature and a calibrated attenuation factor, a temperature of each of at least one object shown in the input thermal image, where the temperature of each of the at least one object is measured independently of the ambient temperature of the radiometric camera.

33 Claims, 4 Drawing Sheets

(51) Int. Cl.

| | |
|---|---|
| *G06T 7/00* | (2017.01) |
| *G06T 5/20* | (2006.01) |
| *G06T 11/60* | (2006.01) |
| *G06T 7/80* | (2017.01) |
| *A61B 5/01* | (2006.01) |
| *A61B 5/00* | (2006.01) |
| *G01J 5/00* | (2022.01) |
| *G06T 5/00* | (2006.01) |
| *G01J 5/80* | (2022.01) |

(52) U.S. Cl.
CPC ............ *A61B 5/7203* (2013.01); *A61B 5/742* (2013.01); *G01J 5/0025* (2013.01); *G06T 5/002* (2013.01); *G06T 5/20* (2013.01); *G06T 7/80* (2017.01); *G06T 11/60* (2013.01); *A61B 2560/0223* (2013.01); *A61B 2560/0252* (2013.01); *G01J 5/80* (2022.01); *G01J 2005/0077* (2013.01); *G06T 2207/10048* (2013.01); *G06T 2207/20182* (2013.01)

(58) Field of Classification Search
USPC .... 382/260, 274, 276, 286, 305, 321; 374/2; 348/211.3, 241; 600/549; 345/589
See application file for complete search history.

(56) References Cited

U.S. PATENT DOCUMENTS

| | | | |
|---|---|---|---|
| 7,936,374 B2* | 5/2011 | Cutler | H04N 5/247 |
| | | | 348/211.3 |
| 7,986,830 B2 | 7/2011 | Lin et al. | |
| 8,111,290 B2* | 2/2012 | Matsushita | H04N 17/002 |
| | | | 345/589 |
| 8,405,746 B2* | 3/2013 | Matsushita | H04N 5/357 |
| | | | 348/241 |
| 8,760,509 B2 | 6/2014 | Schmidt et al. | |
| 8,987,668 B2 | 3/2015 | Vilain et al. | |
| 9,609,180 B2 | 3/2017 | Matsushita et al. | |
| 2008/0154138 A1* | 6/2008 | McQuilkin | G01J 5/0025 |
| | | | 600/549 |
| 2008/0210872 A1 | 9/2008 | Grimberg | |
| 2009/0272888 A1 | 11/2009 | Nugent et al. | |
| 2016/0156880 A1 | 6/2016 | Teich et al. | |
| 2019/0110005 A1* | 4/2019 | Southerland | G01J 5/0806 |

OTHER PUBLICATIONS

Del Pozo, et al., "Vicarious Radiometric Calibration of a Multispectral Camera on Board an Unmanned Aerial System," Remote Sensing, 2014, Spain, pp. 1918-1937.

Hamey, "Radiometric Camera Calibration," Wiley Encyclopedia of Computer Science and Engineering, 2008.

Healey, et al., "Radiometric CCD Camera Calibration and Noise Estimation," IEEE Transactions on Pattern Analysis and Machine Intelligence (vol. 16, Issue: 3), 1994, pp. 267-276, Canada, urL: https://pdfs.semanticscholar.org/6156/f603e50ea74a94779e95b43a4848a9a8642d.pdf.

Kim, et al., "Robust Radiometric Calibration and Vignetting Correction," IEEE Transactions on Pattern Analysis and Machine Intelligence (PAMI), vol. 30, No. 4, Canada, 2008, pp. 562-576.

Lin, et al., "Radiometric Calibration From a Single Image," Proceedings of the 2004 IEEE Computer Society Conference on Computer Vision and Pattern Recognition, CVPR 2004, pp. 1-2.

Mitsunaga, et al., "Radiometric Self Calibration," Proceedings. 1999 IEEE Computer Society Conference on Computer Vision and Pattern Recognition (Cat. No. PR00149), pp. 374-380.

Sentenac, et al., "Temperature Correction of Radiometric and Geometric Models for an Uncooled CCD Camera in the Near Infrared," IEEE Transactions on Instrumentation and Measurement 52(1), 2003, Canada, pp. 1-18.

International Search Report and Written Opinion of International Searching Authority for PCT/US2020/031166, ISA/RU, Moscow, Russia, dated Jan. 12, 2021.

* cited by examiner

THERMAL CAMERA, AND METHOD THEREOF FOR EARLY DIAGNOSIS OF INFECTIOUS DISEASES

TECHNICAL FIELD

The present disclosure relates generally to infrared cameras usable in early diagnosis of infectious diseases.

BACKGROUND

Infectious diseases, such as influenza (flu) or the 2019 novel strain of coronavirus (COVID-19), are caused by viruses. In 2019, the entire world began experiencing the worst pandemic since the 1918 influenza pandemic. To control this pandemic and avoid future outbreaks, new methods and devices are needed to allow early detection and containment of potentially sick people that pose a high risk of transmitting diseases to others.

Detection of people carrying infectious viruses is critical in places with high population density, such as airports, shopping centers, schools, hospitals, and the like. Thus, in order to rapidly detect high risk exposures, detection devices are required to diagnose high volumes of objects (people) in high-traffic areas in real time and with high precision.

One of the symptoms of infectious disease is a high fever. To this end, existing solutions for measuring human body temperatures in crowded areas are based on thermal cameras. Uncooled Bolometric thermal infrared (IR) cameras capture image wavelengths in the range of approximately seven to fourteen micrometers, also known as the long-wave infrared (0) spectrum band. A typical IR camera uses an infrared sensor to detect infrared energy that is guided to the sensor through the camera's lens.

When implementing thermal measurements to obtain body temperature, the technical challenge is the calibration of the camera to achieve accurate measurements. Existing solutions suggest using calibrations based on external and/or internal components. Such components provide a thermal point reference to the measurement.

One example of an external component is a blackbody. A blackbody at thermal equilibrium (a constant temperature) emits electromagnetic radiation called black-body radiation. The radiation has a spectrum that is determined by the temperature alone. An ideal blackbody in thermal equilibrium has two notable properties: those of an ideal emitter and of a diffuse emitter. To achieve higher accuracy, a number of blackbodies are required. That is, the camera needs to be installed together with the blackbodies on site. This requires adjusting and calibrating the location of the blackbodies with respect to the camera, as well as waiting for all the involved temperature sources to stabilize. As such, implementing these solutions complicates the operation of the camera and increases the cost.

It would therefore be advantageous to provide a solution to overcome the challenges noted above.

SUMMARY

A summary of several example embodiments of the disclosure follows. This summary is provided for the convenience of the reader to provide a basic understanding of such embodiments and does not wholly define the breadth of the disclosure. This summary is not an extensive overview of all contemplated embodiments and is intended to neither identify key or critical elements of all embodiments nor to delineate the scope of any or all aspects. Its sole purpose is to present some concepts of one or more embodiments in a simplified form as a prelude to the more detailed description that is presented later. For convenience, the term "certain embodiments" may be used herein to refer to a single embodiment or multiple embodiments of the disclosure.

Certain embodiments disclosed herein include a method for obtaining accurate radiometric readings of objects in a scene captured by a radiometric camera. The method comprises: estimating a gamma drift coefficient based on an input thermal image, wherein the thermal image is captured by an infrared sensor; performing, based on the gamma drift coefficient and the input thermal image, a sensor temperature stabilization to provide an ambient-stabilized thermal image, wherein the ambient-stabilized thermal image is invariant to temperature changes of the infrared sensor; performing ambient calibration to estimate a scene temperature based on the ambient-stabilized thermal image; and measuring, based on the estimated scene temperature and a calibrated attenuation factor, a temperature of each of at least one object shown in the input thermal image, where the temperature of each of the at least one object is measured independently of the ambient temperature of the radiometric camera.

Certain embodiments disclosed herein also include a system for early detection of infectious diseases. The system comprises a radiometric camera configured to display denoised thermal images and accurate radiometric readings of objects seen in the thermal images; a computer connected to the radiometric camera and configured to at least identify objects in the denoised thermal images; and a display connected to the radiometric camera and configured to display the denoised thermal images together with the accurate radiometric readings of objects identified in the thermal images.

Certain embodiments disclosed herein also include an electronic integrated circuit integrated in a radiometric camera and configured to obtaining accurate radiometric readings of objects. The camera comprising: a processing circuitry; and a memory containing instructions that, when executed by the processing circuitry, configure the processing circuitry to: estimate a gamma drift coefficient based on an input thermal image, wherein the thermal image is captured by an infrared sensor; perform, based on the gamma drift coefficient and the input thermal image, a sensor temperature stabilization to provide an ambient-stabilized thermal image, wherein the ambient-stabilized thermal image is invariant to temperature changes of the infrared sensor; perform ambient calibration to estimate a scene temperature based on the ambient-stabilized thermal image; and measure, based on the estimated scene temperature and a calibrated attenuation factor, a temperature of each of at least one object shown in the input thermal image, where the temperature of each of the at least one object is measured independently of the ambient temperature of the radiometric camera.

Certain embodiments disclosed herein also include a radiometric camera, comprising: at least one optical unit including at least one lens; an infrared sensor coupled to the optical unit and configured to capture thermal images; and an integrated circuit (IC) configured to process the captured thermal images to output obtaining accurate radiometric readings of objects seen in the thermal images, wherein the IC further comprises: a processing circuitry; and a memory containing instructions that, when executed by the processing circuitry, configure the processing circuitry to: estimate a gamma drift coefficient based on an input thermal image, wherein the thermal image is captured by an infrared sensor; perform, based on the gamma drift coefficient and the input thermal image, a sensor temperature stabilization to provide an ambient-stabilized thermal image, wherein the ambient-stabilized thermal image is invariant to temperature changes of the infrared sensor; perform ambient calibration to estimate a scene temperature based on the ambient-stabilized thermal image; and measure, based on the estimated scene temperature and a calibrated attenuation factor, a temperature of each of at least one object shown in the input thermal image, where the temperature of each of the at least one object is measured independently of the ambient temperature of the radiometric camera.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
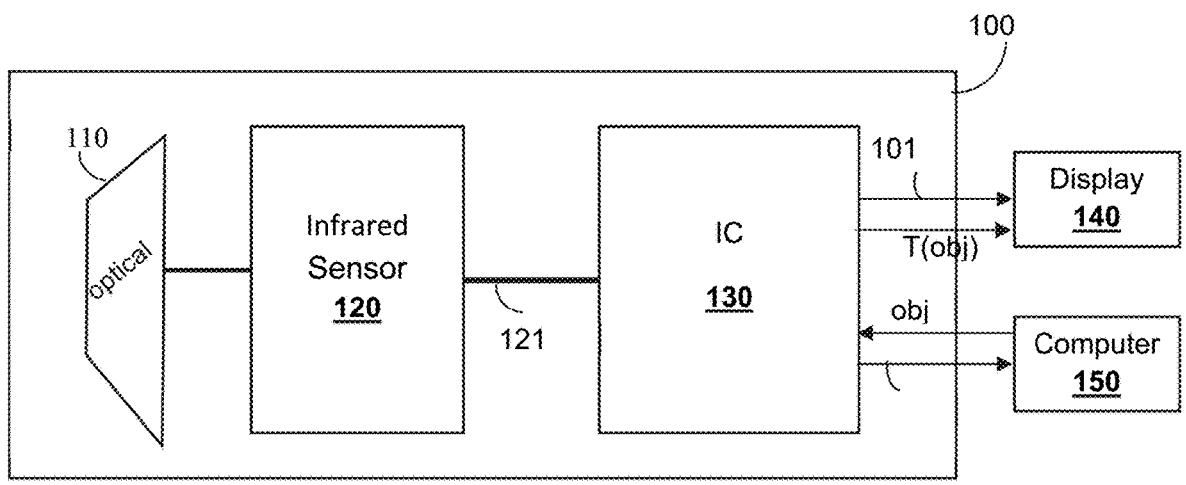
FIG. 1 shows a block diagram of a high throughput radiometric camera, utilized to describe the various disclosed embodiments.

It is important to note that the embodiments disclosed herein are only examples of the many advantageous uses of the innovative teachings herein. In general, statements made in the specification of the present application do not necessarily limit any of the various claimed embodiments. Moreover, some statements may apply to some inventive features but not to others. In general, unless otherwise indicated, singular elements may be in plural and vice versa with no loss of generality. In the drawings, like numerals refer to like parts through several views.

The disclosed embodiments include techniques for detecting symptoms of infectious diseases using a high throughput radiometric camera. The radiometric camera is designed to provide simultaneous accurate body temperature measurements for multiple objects in a crowded area. In an example implementation, such objects include people. The accurate measurements are achieved by correcting fixed pattern noises (FPNs) and determining a gamma drift reference. The gamma drift reference is the amount of drift during the camera operation. The gamma drift reference provides a reference for body temperature measurements, thereby eliminating the need to use external blackbodies. In at least some disclosed embodiments, no shutter is used in the throughput radiometric camera. Therefore, no internal physical element needs to be used as a temperature reference signal (point).

FIG. 1 shows an example block diagram of a high throughput radiometric camera (hereinafter, the "camera 100") designed according to the various disclosed embodiments. The camera 100 includes an optical unit 110 and an infrared sensor 120 coupled to an integrated circuit (IC) 130. The output of the radiometric camera 100 is a video stream of thermal images (hereinafter a "thermal video stream") captured by the infrared sensor 120 and processed by the IC 130.

The thermal video stream is interposed with body temperature measurements and displayed together on a display 140. The display 140 may be external to the camera 100. In another embodiment, the display may be an LCD screen encapsulated in the same housing (not shown) of the camera 100. The body temperature measurements are presented with respect to each object identified in the thermal image. In an example implementation, the body temperature measurements may be presented using boxes around the object. The measurements may be presented as a numerical value, a color-coded indication, or both.

In an embodiment, the infrared sensor 120 is an uncooled long-wavelength infrared (LWIR) sensor, operating in a spectrum band of wavelengths of 7-14 μm. The spectrum of passive heat emission by a human body, predicted by Planck's law at 305 K, greatly overlaps with the LWIR spectrum band. Thus, a high-resolution LWIR cameras and sensors are a good choice for designing high-throughput temperature screening solutions for human subjects. An uncooled sensor having a small form factor can typically be mass-produced using low-cost technology. The infrared sensor 120 includes, or is realized as, a focal plane array (FPA). An FPA produces a reference signal utilized to derive temperature information from the thermal image signal. In some configurations, the sensor 120 and the FPA (not shown) are the same unit and are collectively referred to hereinafter as the "infrared sensor 120."

The camera 100 outputs a thermal image stream 101 of denoised thermal images, fed into a computer 150 and a display 140. As will be discussed below with reference to FIG. 2, to measure a temperature of an object, the IC 130 is configured to estimate the gamma drift offset and to subsequently neutralize the effect of changes in the sensor's 120 FPA temperature based on this drift so that normalized readings for different temperatures of the FPA can be recorded. The FPA temperature is the temperature in the vicinity of the FPA and sensor 120. The FPA temperature stabilization process results in a pixel response signal (Is). The IC 130 is further configured to determine the scene temperature value (Ts). The Ts value is used, in part, by a radiometric process that is also performed by the IC 130, to determine the temperature of objects in the scene (current denoised image).

The computer 150 is configured to perform at least a perception process. The perception process is configured to identify objects (e.g., persons) in input images. In an embodiment, the identified object is a person and the measured temperature is a human body temperature. The computer 150 may receive environmental data related to, for example, an ambient temperature, a current measured room (e.g., an office), temperature, humidity information, and the like. To this end, the computer 150 may interface with HVAC controllers, wireless thermostats, and the like. Such data may be provided to the camera 100 to be utilized in the radiometry process.

The computer 150 may be any computing device or unit including a processing circuitry (not shown) coupled to a memory (not shown), an I/O interface (not shown), and a network interface (not shown). The processing circuitry may be realized as one or more hardware logic components and circuits. For example, and without limitation, illustrative types of hardware logic components that can be used include field programmable gate arrays (FPGAs), application-specific integrated circuits (ASICs), application-specific standard products (ASSPs), system-on-a-chip systems (SoCs), general-purpose microprocessors, microcontrollers, digital signal processors (DSPs), and the like, or any other hardware logic components that can perform calculations or other manipulations of information. The memory may be, for example, a flash memory, or any type of non-volatile memory.

In an embodiment, the perception and radiometry processes may be implemented or performed by the IC 130. Thus, in such configurations, the computer 150 is not required. In another embodiment, the computer 150 and the camera 100 are part of a radiometric system.

In one configuration, the optical unit 110 includes one or more lens elements (not shown), each of which having a predetermined field of view (FoV). In an embodiment, the lens elements may be made of chalcogenide.

In an example configuration, the infrared sensor 120 is coupled through a communication bus 121 to the IC 130 to input the captured thermal images, metadata, and other control signals (e.g., clock, synchronization, and the like).

Figure 2:
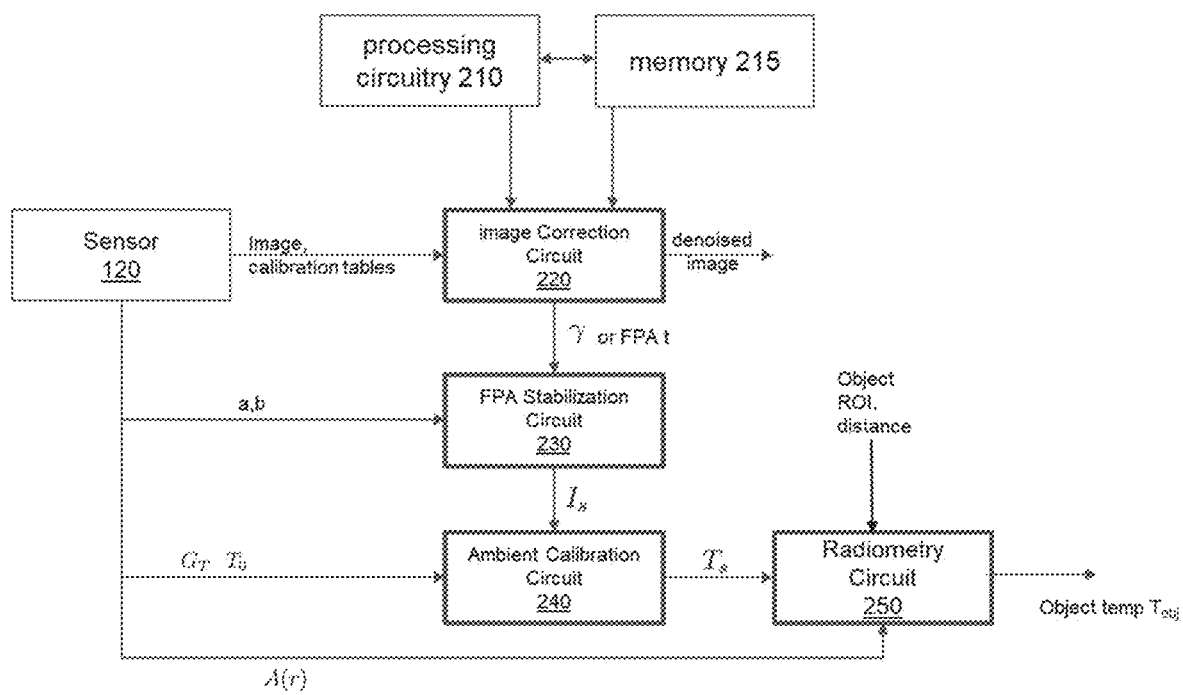
FIG. 2 shows a block diagram of the IC shown in FIG. 1, designed according to an embodiment.

The IC 130 includes a memory, a processing circuitry, and various circuits and modules allowing the execution of the tasks noted herein. A detailed block diagram of the IC 130 is shown in FIG. 2. The IC 130 may be realized as a chipset, a SoC, a FPGA, a PLD, an ASIC, or any other type of digital and/or analog hardware components.

According to the disclosed embodiments, the temperature measurements are performed without any external blackbody and without using a shutter as a reference point. Rather, temperature measurements may be based, in part, on a gamma-based drift measurement algorithm that outputs the amount of drift during the camera's 100 operation. The changes in the infrared sensor's 120 temperature creates offsets that may be different from pixel to pixel. Therefore, in addition to a common (DC) drift component, there is a fixed pattern noise that is added to each image. In an embodiment, the IC 130 is configured to measure the fixed-noise pattern during the camera's 100 calibration and estimate the amount of the gamma drift during operation.

The camera 100 is calibrated during manufacturing (e.g., at a lab) prior to operation. The calibration process is performed to stabilize the camera 100 at a predefined temperature. The calibration process includes reading the ambient temperature, which is periodically read from the sensor 120 to determine temperature stability.

In an example configuration, the sensor 120 and IC 130 are encapsulated in a thermal core (not shown). The thermal core is utilized to ensure a uniform temperature for the camera 100. The temperature calibration of the thermal core is also factory calibration. The optical unit 110 is typically assembled in the camera 100 after the infrared sensor 120 and IC 130 are encapsulated in the thermal core.

As will be discussed below, the processing performed by the IC 130 enhances the quality of the captured thermal images to allow for the accurate and fast detection of objects (e.g., persons). To this end, the IC 130 may be configured to perform one or more image processing tasks, such as shutterless correction of the captured thermal images, and correction of fixed pattern noise due to ambient drift. As demonstrated in FIG. 1, the camera 100 does not include a shutter (or any moving part that can be viewed as shutter). To this end, the IC 130 may be configured to execute shutterless image correction for the performance of a flat-field correction without a shutter. That is, shutterless correction allows for a radiometry image with unwanted fixed pattern noise removed therefrom.

In yet another embodiment, the camera 100 includes a shutter (or any equivalent moving part). Using a shutter can be used for improved noise reduction that may be required in static cameras, as well as increasing uniformity in the image-based temperature sensing.

The radiometric system, illustrated in FIG. 1, includes the radiometric camera 100 the display 140 and the computer 150 an provide early diagnosis system for infectious diseases, such as influenza, coronavirus, severe acute respiratory syndrome, and the like. One of the common symptoms of such diseases is fever. Thus, by providing a system that can accurately measure body temperature, the disclosed embodiments allow for providing early diagnoses of fever, and thus indication on sickness, or infectious diseases. Furthermore, due to the ability of the radiometric camera 100 to measure temperature of many people simultaneously, the system can be installed in areas with high traffic of people, such as airports, stadiums, train stations, and the like.

FIG. 2 shows an example block diagram of the IC 130, designed according to an embodiment. The IC 130 includes a processing circuitry 210 coupled to a memory 215, an image correction circuit 220, an FPA stabilization circuit 230, an ambient calibration circuit 240, and a radiometric circuit 250.

The IC 130 interfaces with the external elements, such as the display 140 and computer 150 of FIG. 1 (not shown in FIG. 2), via, for example, a multimedia link. In an example embodiment, the multimedia link is a gigabit multimedia serial link (GMSL). The image correction circuit 220 outputs the denoised image streams to the display 140.

In an embodiment, the memory 215 is configured to store calibration tables. The calibration tables include calibration values for each pixel computed in the lab. The calibration values may include gain and offset values calculated from two temperature points ($T_1$, $T_2$) for the purpose of overcoming the irregularities in the infrared sensor (120, FIG. 1) and unifying the pixels' response to infrared radiation for a normal ambient room temperature. The calibration tables also include a drift value determined for each pixel at a room temperature point during the calibration process. In an embodiment, the calibration tables also store various parameter values which may be applied to set the radiometric camera 100.

The memory 215 may further store computer readable instructions to be executed by the processing circuitry 210 and by the circuits 220, 230, 240, and 250. Computer readable instructions shall be construed broadly to mean any type of instructions, whether referred to as software, firmware, middleware, microcode, hardware description language, or otherwise. Instructions may include code (e.g., in source code format, binary code format, executable code format, or any other suitable format of code). The instructions, when executed by the processing circuitry and circuits, cause these processors to perform the various embodiments and tasks described herein. The memory 215 may be volatile (e.g., RAM, etc.), non-volatile (e.g., ROM, flash memory, etc.), or a combination thereof.

The processing circuitry 210 is configured to control the various elements of the IC 130. The processing circuitry 210 is further configured to power-up the infrared sensor (FIG. 1, 120) and to upload the initial calibration tables.

The image correction circuit 220 is configured to perform at least gamma drift correction and estimate a current gamma drift coefficient $\gamma$. The gamma drift correction may be for each pixel in a received thermal image.

In an embodiment, the gamma drift correction is based on estimating a drift coefficient γ using a drift pattern (table) recorded during the calibration of the sensor 120. In an embodiment, estimation of the gamma drift coefficient γ is performed iteratively with small incremental updates based on each input image, so that any residual noise (or new noise, if the ambient temperature changes) is detected and removed with each subsequent image.

The estimated gamma drift coefficient, γ, used for the correction is derived from the drift pattern from the initial calibration and the resulting pattern of drift within an input image after a high pass filter has been applied thereto.

A generalized equation for estimating the gamma drift coefficient, γ, is the quotient of the product of the drift pattern and the input image pixel values after applying a high pass filter thereto, and the product of the drift pattern and the drift pattern after applying a high pass filter thereto, represented by the following equation:

$$\gamma = \frac{\langle H_1(D), H_2(I_{in}) \rangle}{\langle H_1(D), H_2(D) \rangle} \qquad \text{Equation 1}$$

where $H_1$ and $H_2$ are pre-processing operators designed to minimize correlation between a clean image of the scene and the drift pattern, $I_{in}$ is a captured image, and D is the drift pattern calibrated at the time of manufacture of the camera. Without loss of generality, the $H_1$ and $H_2$ operators may include high pass filtering and masking. An example of such operations, without loss of generality, can be $H_1$=identity map and $H_2$=a high-pass filter. In Equation 1, γ is a scalar value obtained as a ratio of 2 inner products. Therefore, it is one value for all pixels at this stage.

The denoised (clean) images are generated by removing the drift from input images. That is, the denoised images are generated by subtracting a calibrated drift pattern multiplied by the estimated gamma drift coefficient γ from each pixel in the input image. In some embodiments, the gain and offset are corrected in an input image, prior to the drift correction. The gain and offset correction may be performed by the processing circuitry 210. Further, a 2-point correction to remove fixed pattern noise from the received thermal images may be performed as well.

The gamma drift coefficient, γ, is fed into the FPA stabilization circuit 230. The circuit 230 is configured to neutralize the effect of changes in the FPA's temperatures and to return the same result for different FPA temperatures (i.e., it is FPA-invariant). The circuit 230 outputs an ambient-stabilized image $I_s$. In an embodiment, the ambient-stabilized image $I_s$ is estimated using the following equation:

$$I_s = I - \alpha\gamma - b; \qquad \text{Equation 2}$$

where 'a' and 'b' are the linear coefficients which must be calibrated to produce an ambient-stabilized image $I_s$, I is the input image, and where γ is the gamma drift coefficient provided by the circuit 220. In an embodiment, the calibration of the 'a' and 'b' coefficients is performed in a temperature-control chamber.

In some embodiments, the gamma drift coefficient in Equation 2 can be replaced with a linear readout of a current thermal value of the FPA (or thermal diode at the sensor). The ambient-stabilized image $I_s$ is fed into the ambient calibration circuit 240. The ambient calibration circuit 240 is configured to translate the ambient-stabilized image $I_s$ into temperature units. In an embodiment, this is achieved by the following linear translation function:

$$T_s = G_T I_s + T_0 \qquad \text{Equation 3}$$

where, $T_s$ is the output temperature of the entire scene in temperature units (e.g., Celsius), $G_T$ is a gain constant that translates changes in pixel values in the scene (denoted by $I_s$) into changes in temperature units, and $T_0$ is a predefined nominal temperature offset. The gain constant $G_T$ and the temperature offset $T_0$ are determined, for example, during manufacturing calibration of the camera. In example implementation, the temperature offset $T_0$ is set to 30° C. It should be noted that the linear relationship defined in Equations 2 and 3 is valid within a limited ambient temperature range (for example, between 20° C.-30° C.). If the camera 100 is installed in areas with ambient temperature different from the range noted above, the linear relationship defined in Eq. 2 and Eq. 3 will be calibrated or defined using non-linear equations.

Once the $T_s$ is calibrated, the camera 100 can output real ambient temperatures independent of the camera temperature. The scene temperature $T_s$ is fed to the radiometric circuitry 250.

The radiometric circuitry 250 receives, from the computer (150, FIG. 1), at least a list of objects (humans) identified in the scene. The computer 150 may further provide a distance between objects in the scene and the camera, and environment data that can be utilized to estimate changes in the ambient temperature.

In an embodiment, the attenuation factor A(r) of the sensor is calibrated. This factor corresponds to the reduced capability of the camera to sense the difference between the object temperature and the ambient temperature (e.g., differences due to environmental and other reasons such as a reduced object size smaller than pixel, reduced object emissivity [less than 1], medium absorption, etc.). The attenuation factor A(r) may be calibrated to increase temperature measurement precision for objects of certain types and at certain ranges during the manufacturing of the camera 100.

The radiometric circuit 250 is configured to measure the temperature of some or all objects listed in the list of objects provided by the computer 150. The temperature is provided individually for each measured object ($T_{obj}$).

In an embodiment, the radiometric circuit 250 measures an object temperature based on the following equation:

$$T_{obj} = \frac{1}{A(r)}[G_T I_s + T_0 - T_{amb}(1 - A(r))] \qquad \text{Equation 4}$$

where, $T_{amb}$ is the ambient temperature, and the rest of the parameters in Equation 4 are defined above. In this regard, it has been identified that, when measuring the body temperature, the temperature at the face (or forehead) is important as typically being indicative of the health of the person. In an embodiment, the ambient temperature is modulated, and can be replaced by another background temperature. For example, if one is interested to measure the temperature of eye areas, the eye background can be modeled by the face temperature with some difference in the temperature, as follows:

$$T_{eye} = T_{face} + \Delta T \qquad \text{Equation 5}$$

The temperature at the eyes ($T_{eye}$) of an object (human) are measured as follows:

$$T_{eye} = G_T I_S + T_0 - \Delta T(A(r) - 1) \qquad \text{Equation 6}$$

It should be noted that all the parameters (a, b, GT, T0, and A(r)) which are calibrated during manufacturing are stored in the memory 215 and can be retrieved by the various circuits during operation of the camera. The calibration of the parameters (a, b, GT, T0, D, and A(r)) may be at only two temperature points, e.g., 30° C. and 32° C. It should be further noted that the eye temperature discussed above is merely an example of determining a temperature for a specific area on the identified object (e.g., a specific part of the human body), and that the disclosed embodiments may be equally applicable to other areas.

It should be noted that each of the each of the circuits 220 through 250 may be realized as one or more hardware logic components and circuits. For example, and without limitation, illustrative types of hardware logic components are provided above. In some configurations, the circuits 220 through 250 are implemented in a single SoC or as part of the processing circuitry 210.

Figure 3:
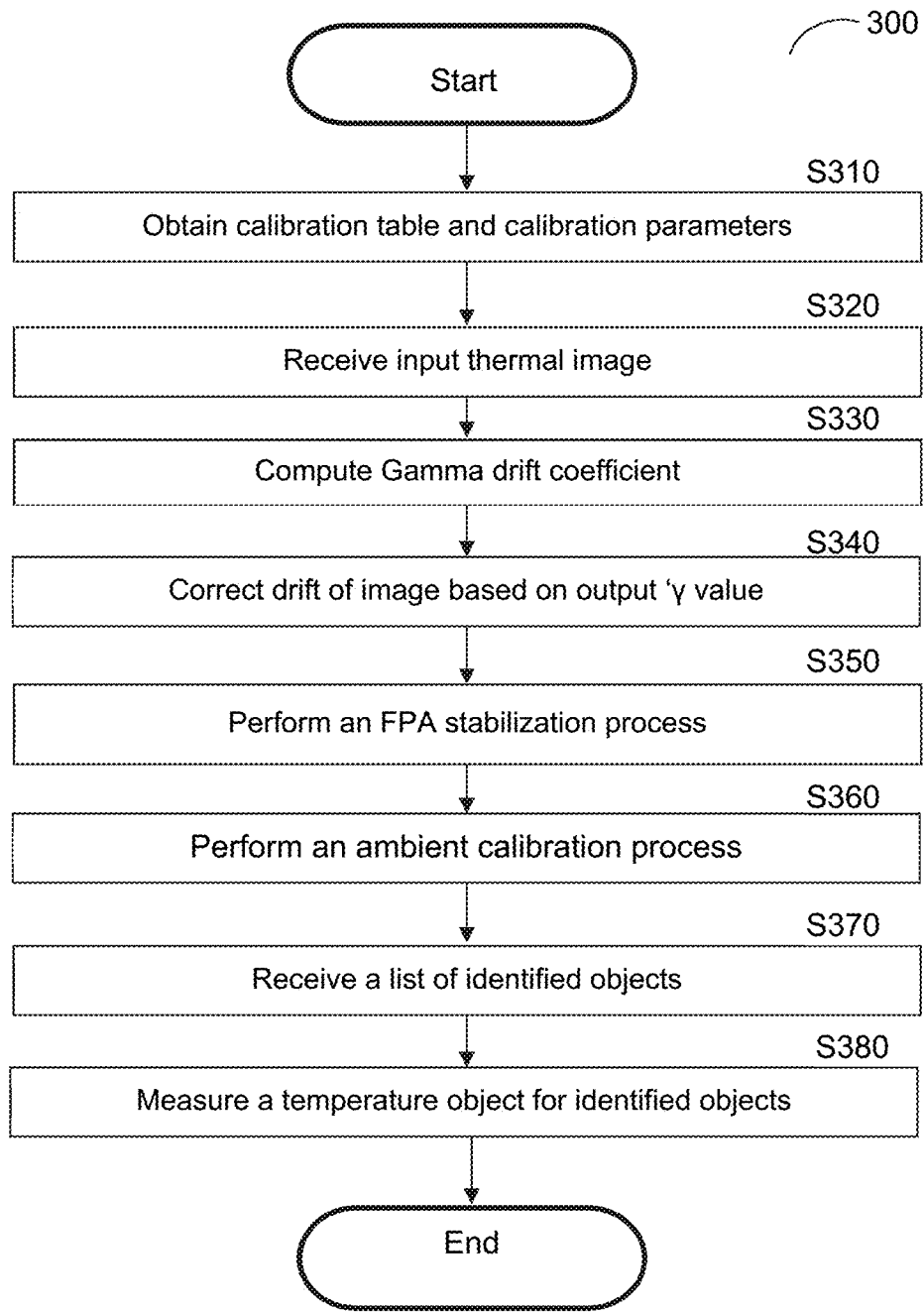
FIG. 3 shows a flowchart illustrating a method for obtaining accurate radiometric readings of multiple objects simultaneously, according to an embodiment.

FIG. 3 shows an example flowchart 300 illustrating a method for obtaining accurate radiometric readings of multiple objects simultaneously, according to an embodiment.

At S310, a sensor calibration table and parameters are obtained. In an embodiment, the calibration table includes calibrated values for each pixel of the infrared sensor. For example, calibrated values may represent the amount of anticipated gain (G), offset (O), and drift (D) associated with each pixel under certain conditions, e.g., adjustment values that are associated with specific ambient temperatures. In an embodiment, specific ambient temperatures include room temperature. The calibration parameters may include the attenuation factor A(r), linear calibration values a and b, and a predefined nominal temperature T0. The calibration table and parameters may be stored in a memory or database that is remotely or locally accessible.

At S320, a thermal image is received from the infrared sensor, e.g., the sensor 120 of FIG. 1, above. At S330, a gamma drift coefficient γ is computed for the received image. In an embodiment, Equation 1 is utilized to compute the gamma drift coefficient.

At S340, the value of the gamma drift coefficient, γ, is applied to the input image to correct the drift gain from the image. In an optional embodiment, S340 includes applying a 2-point correction on each input thermal image to remove fixed-noise patterns. The output of S340 is a denoised image sent to a display and a perception process. The perception process identifies objects in the denoised image. It should be noted that any visual recognition process applicable to identified objects in thermal images can be utilized in accordance with the disclosed embodiments.

At S350, an FPA temperature stabilization process is performed to ensure that the sensor and, hence, the camera output, becomes invariant to changes in the FPA's temperature. As noted above, the output of S350 is an ambient-stabilized thermal image, $I_s$, responsive to the input image. In an embodiment, the ambient-stabilized thermal image, $I_s$, is provided based on the gamma drift coefficient, γ, and the linear calibration parameters a and b, as shown, for example, in Equation 2. As noted above, the model defined by Equation 2 can be replaced by a non-linear relationship model).

At S360, an ambient calibration process is performed to estimate a scene temperature (TS) for the scene shown in the received input image. In an embodiment, the estimation of the temperature (TS) is performed based on the ambient-stabilized image $I_s$, the gain constant $G_T$, and the temperature offset $T_0$ as shown, for example, in Equation 3. As noted above, the model defined by Equation 2 can be replaced by a non-linear relationship model).

At S370, a list of objects identified in the denoised thermal image, together with the distance of each object from the camera, is received. At S380, the temperature ($T_{obj}$) of some or all of the objects in the received list is measured. An object temperature ($T_{obj}$) is measured independently of the ambient temperature of the camera. In an embodiment, the object temperature is measured, in part, using the scene temperature ($T_S$) and a calibrated attenuation factor (A(r)). In an embodiment, an object temperature may be not measured for an object when the object's distance from the camera is above a predefined threshold.

The measured object temperatures are displayed next to each respective object overlaid in the denoised image.

Figure 4:
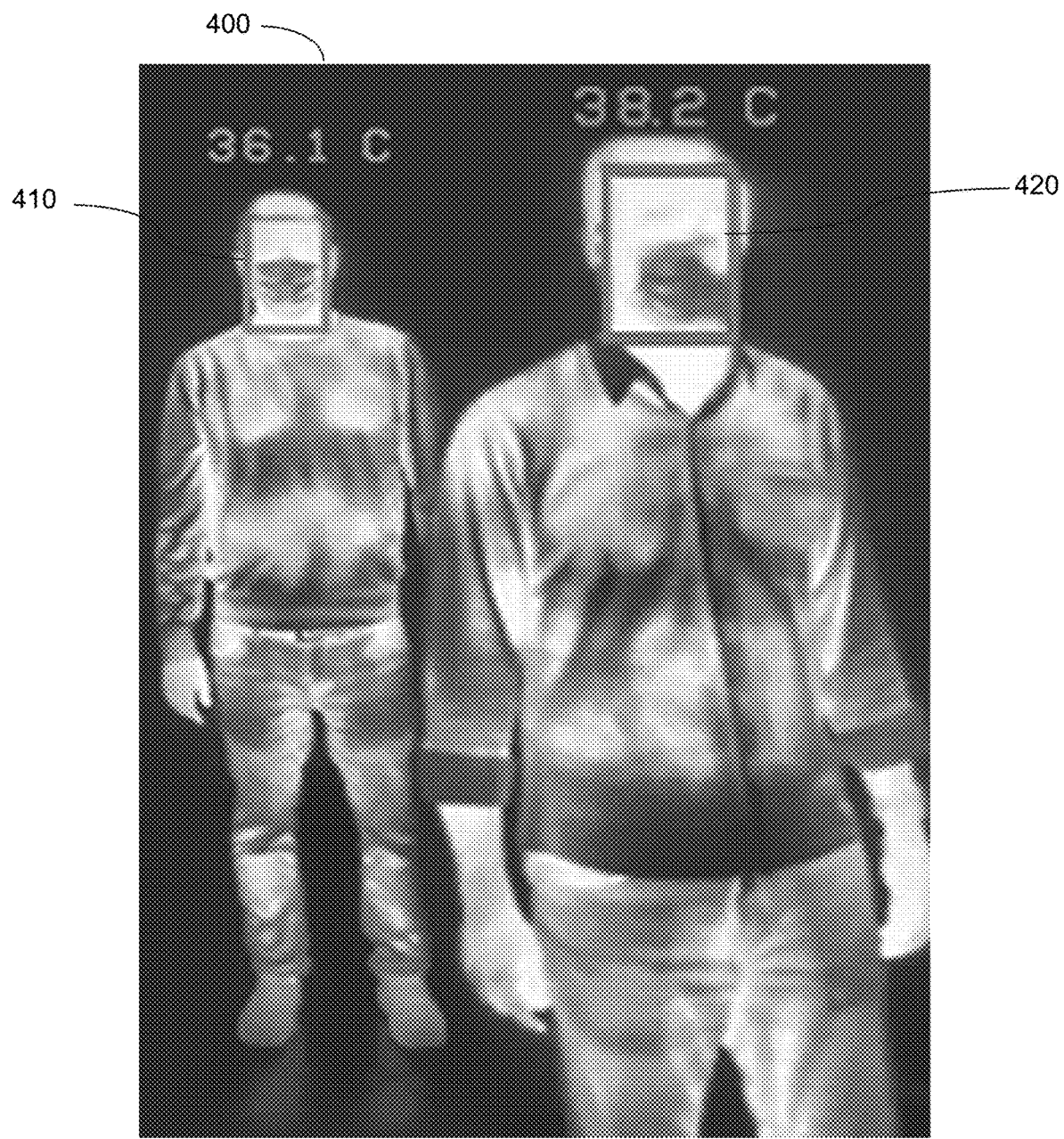
FIG. 4 shows an example output denoised image, applicable to identify objects.

FIG. 4 shows an example output denoised image 400, applicable to identify persons (objects) 410 and 420. Next to each person 410 or 420, the respective temperature is displayed. The displayed temperature may be color-coded, for example, the person 420 may be boxed with a red box, while the person 410 may be boxed with a green box.

The various embodiments disclosed herein can be implemented as hardware, firmware, software, or any combination thereof. Moreover, the software is preferably implemented as an application program tangibly embodied on a program storage unit or computer readable medium consisting of parts, or of certain devices and/or a combination of devices. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such a computer or processor is explicitly shown. In addition, various other peripheral units may be connected to the computer platform, such as an additional data storage unit and a printing unit. Furthermore, a non-transitory computer readable medium is any computer readable medium except for a transitory propagating signal.

As used herein, the phrase "at least one of" followed by a listing of items means that any of the listed items can be utilized individually, or any combination of two or more of the listed items can be utilized. For example, if a system is described as including "at least one of A, B, and C," the system can include A alone; B alone; C alone; A and B in combination; B and C in combination; A and C in combination; or A, B, and C in combination.

It should be understood that any reference to an element herein using a designation such as "first," "second," and so forth does not generally limit the quantity or order of those elements. Rather, these designations are generally used herein as a convenient method of distinguishing between two or more elements or instances of an element. Thus, a reference to first and second elements does not mean that only two elements may be employed there or that the first element must precede the second element in some manner. Also, unless stated otherwise, a set of elements comprises one or more elements.

All examples and conditional language recited herein are intended for pedagogical purposes to aid the reader in understanding the principles of the disclosed embodiment and the concepts contributed by the inventor to furthering the art, and are to be construed as being without limitation to such specifically recited examples and conditions. Moreover, all statements herein reciting principles, aspects, and embodiments of the disclosed embodiments, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

What is claimed is:

1. A method for obtaining accurate radiometric readings of objects in a scene captured by a radiometric camera, comprising:
   estimating a gamma drift coefficient based on an input thermal image, wherein the thermal image is captured by an infrared sensor;
   performing, based on the gamma drift coefficient and the input thermal image, a sensor temperature stabilization to provide an ambient-stabilized thermal image, wherein the ambient-stabilized thermal image is invariant to temperature changes of the infrared sensor;
   performing ambient calibration to estimate a scene temperature based on the ambient-stabilized thermal image; and
   measuring, based on the estimated scene temperature and a calibrated attenuation factor, a temperature of each of at least one object shown in the input thermal image, where the temperature of each of the at least one object is measured independently of the ambient temperature of the radiometric camera; and
   estimating the ambient-stabilized thermal image based on the input thermal image, a pair of linear coefficients, and the estimated gamma drift coefficient, wherein the pair of linear coefficients are factory-calibrated coefficients, wherein the ambient-stabilized thermal image is invariant to temperature changes of a focal point array of the infrared sensor.

2. The method of claim 1, further comprising:
   obtaining a sensor calibration table and a plurality of calibration parameters, wherein the sensor calibration table includes calibrated values for each pixel of the infrared sensor, wherein the plurality of calibration parameters include a calibrated attenuation factor linear calibration values used for the sensor temperature stabilization, and a predefined nominal temperature used for the ambient calibration.

3. The method of claim 1, further comprising:
   correcting the input thermal image by removing gamma drift from the input thermal image and removing fixed-noise patterns, wherein the gamma drift is determined based on the gamma drift coefficient.

4. The method of claim 3, further comprising:
   identifying the at least one object in the corrected input thermal image, wherein the at least one object is identified using a perception process.

5. The method of claim 1, wherein measuring the temperature of each of the at least one object shown in the input thermal image further comprises:
   simultaneously measuring an object temperature of each of the at least one object.

6. The method of claim 1, wherein each of the at least one object is a human, wherein the measured temperature of each of the at least one object is a body temperature.

7. The method of claim 1, wherein estimating the gamma drift coefficient further comprises:
   filtering the input image by applying a high pass filter to the input image; and
   deriving the gamma drift coefficient based on a drift pattern within the filtered input image.

8. The method of claim 1, wherein performing the ambient calibration further comprises:
   translating an ambient-stabilized image into temperature units of the scene using a linear translation function.

9. The method of claim 8, wherein the linear translation function is based on the ambient-stabilized thermal image, a predefined nominal temperature offset, and a gain constant translating changes in pixel values in the scene into changes in temperature units.

10. The method of claim 9, wherein measuring the temperature of at least one object identified in the input thermal image further comprises:
    modeling the ambient temperature as a temperature of a specific pixeled area in the at least one identified object.

11. The method of claim 10, wherein each the at least one identified object is a human, wherein the specific pixeled area is the human eyes.

12. The method of claim 11, wherein the temperature at the eyes are modeled using the following equation: $T_{eye} = G_T I_S + T_0 - \Delta T(A(r) - 1)$, wherein $T_{eye}$ is the temperature at the eyes, $G_T$ is a gain constant, $I_s$ is the ambient-stabilized image, and $T_0$ is a predefined nominal temperature offset.

13. The method of claim 1, wherein the infrared sensor operates in a long-wave infrared (LWIR) spectrum band.

14. The method of claim 1, wherein the radiometric camera operates in a system for early detection of infectious diseases.

15. A non-transitory computer readable medium having stored thereon instructions for causing a processing circuitry to perform the method of claim 12.

16. An electronic circuit integrated in a radiometric camera and configured to obtaining accurate radiometric readings of objects, comprising:
    a processing circuitry; and
    a memory containing instructions that, when executed by the processing circuitry, configure the processing circuitry to:
    estimate a gamma drift coefficient based on an input thermal image, wherein the thermal image is captured by an infrared sensor;
    perform, based on the gamma drift coefficient and the input thermal image, a sensor temperature stabilization to provide an ambient-stabilized thermal image, wherein the ambient-stabilized thermal image is invariant to temperature changes of the infrared sensor;
    perform ambient calibration to estimate a scene temperature based on the ambient-stabilized thermal image; and
    measure, based on the estimated scene temperature and a calibrated attenuation factor, a temperature of each of at least one object shown in the input thermal image, where the temperature of each of the at least one object is measured independently of the ambient temperature of the radiometric camera; and
    estimate the ambient-stabilized thermal image based on the input thermal image, a pair of linear coefficients, and the estimated gamma drift coefficient, wherein the pair of linear coefficients are factory-calibrated coefficients, wherein the ambient-stabilized thermal image is invariant to temperature changes of a focal point array of the infrared sensor.

17. A radiometric camera, comprising:
    at least one optical unit including at least one lens;
    an infrared sensor coupled to the optical unit and configured to capture thermal images; and
    an integrated circuit (IC) configured to process the captured thermal images to output obtaining accurate radiometric readings of objects seen in the thermal images, wherein the IC further comprises:

a processing circuitry; and a memory containing instructions that, when executed by the processing circuitry, configure the processing circuitry to:

estimate a gamma drift coefficient based on an input thermal image, wherein the thermal image is captured by an infrared sensor;

perform, based on the gamma drift coefficient and the input thermal image, a sensor temperature stabilization to provide an ambient-stabilized thermal image, wherein the ambient-stabilized thermal image is invariant to temperature changes of the infrared sensor;

perform ambient calibration to estimate a scene temperature based on the ambient-stabilized thermal image; and measure, based on the estimated scene temperature and a calibrated attenuation factor, a temperature of each of at least one object shown in the input thermal image, where the temperature of each of the at least one object is measured independently of the ambient temperature of the radiometric camera; and estimate the ambient-stabilized thermal image based on the input thermal image, a pair of linear coefficients, and the estimated gamma drift coefficient, wherein the pair of linear coefficients are factory-calibrated coefficients, wherein the ambient-stabilized thermal image is invariant to temperature changes of a focal point array of the infrared sensor.

18. The radiometric camera of claim 17, wherein the radiometric camera is a shutterless camera.

19. The radiometric camera of claim 17, wherein the radiometric camera operates in a system for early infectious diseases detection.

20. The radiometric camera of claim 17, wherein the IC further comprises:

obtain a sensor calibration table and a plurality of calibration parameters, wherein the sensor calibration table includes calibrated values for each pixel of the infrared sensor, wherein the plurality of calibration parameters include a calibrated attenuation factor linear calibration values used for the sensor temperature stabilization, and a predefined nominal temperature used for the ambient calibration.

21. The radiometric camera of claim 17, wherein the IC further comprises:

correct the input thermal image by removing gamma drift from the input thermal image and removing fixed-noise patterns, wherein the gamma drift is determined based on the gamma drift coefficient.

22. The radiometric camera of claim 21, wherein the IC further comprises:

identify the at least one object in the corrected input thermal image, wherein the at least one object is identified using a perception process.

23. The radiometric camera of claim 17, wherein the IC further comprises:

simultaneously measure an object temperature of each of the at least one object.

24. The radiometric camera of claim 17, wherein each of the at least one object is a human, wherein the measured temperature of each of the at least one object is a body temperature.

25. The radiometric camera of claim 17, wherein the IC further comprises:

filter the input image by applying a high pass filter to the input image; and derive the gamma drift coefficient based on a drift pattern within the filtered input image.

26. The radiometric camera of claim 17, wherein the IC further comprises:

estimate the ambient-stabilized thermal image based on the input thermal image, a pair of linear coefficients, and the estimated gamma drift coefficient, wherein the pair of linear coefficients are factory-calibrated coefficients.

27. The radiometric camera of claim 26, wherein the ambient-stabilized thermal image is invariant to temperature changes of a focal point array of the infrared sensor.

28. The radiometric camera of claim 17, wherein the IC further comprises:

translate an ambient-stabilized image into temperature units of the scene using a linear translation function.

29. The radiometric camera of claim 28, wherein the linear translation function is based on the ambient-stabilized thermal image, a predefined nominal temperature offset, and a gain constant translating changes in pixel values in the scene into changes in temperature units.

30. The radiometric camera of claim 29, wherein the temperature at the eyes are modeled using the following equation: $T_{eye}=G_T I_S+T_0-\Delta T(A(r)-1)$, wherein $T_{eye}$ is the temperature at the eyes, $G_T$ is a gain constant, $I_s$ is the ambient-stabilized image, and $T_0$ is a predefined nominal temperature offset.

31. The radiometric camera of claim 28, wherein the IC further comprises:

model the ambient temperature as a temperature of a specific pixeled area in the at least one object.

32. The radiometric camera of claim 31, wherein each the at least one object is a human, wherein the specific pixeled area is the human eyes.

33. The radiometric camera of claim 17, wherein the infrared sensor operates in a long-wave infrared (LWIR) spectrum band.

* * * * *